(12) United States Patent
Pandey et al.

(10) Patent No.: US 7,078,014 B2
(45) Date of Patent: Jul. 18, 2006

(54) METHOD FOR USING CHLORIN AND BACTERIOCHLORIN-BASED AMINOPHENYL DTPA AND $N_2S_2$ CONJUGATES FOR MR CONTRAST MEDIA AND RADIOPHARMACEUTICALS

(75) Inventors: Ravindra K. Pandey, Williamsville, NY (US); Zachary Grossman, Buffalo, NY (US); Peter Kanter, East Aurora, NY (US); Thomas J. Dougherty, Grand Island, NY (US)

(73) Assignee: Health Research, Inc., Buffalo, NY (US)

( * ) Notice: Subject to any disclaimer, the term of this patent is extended or adjusted under 35 U.S.C. 154(b) by 211 days.

(21) Appl. No.: 10/390,438

(22) Filed: Mar. 17, 2003

(65) Prior Publication Data

US 2004/0022737 A1 Feb. 5, 2004

Related U.S. Application Data

(63) Continuation-in-part of application No. 09/739,155, filed on Dec. 18, 2000, now Pat. No. 6,534,040.

(60) Provisional application No. 60/171,961, filed on Dec. 23, 1999.

(51) Int. Cl.
*A61B 5/055* (2006.01)

(52) U.S. Cl. .................. 424/9.3; 424/1.11; 424/1.65; 424/9.1; 540/145

(58) Field of Classification Search ............. 424/1.11, 424/1.65, 9.1, 9.3, 9.32, 9.35, 9.36, 9.361, 424/9.363, 9.37, 9.362, 9.6; 540/145
See application file for complete search history.

(56) References Cited

U.S. PATENT DOCUMENTS

| | | | |
|---|---|---|---|
| 4,649,151 A | 3/1987 | Dougherty et al. | |
| 4,866,168 A | 9/1989 | Dougherty et al. | |
| 4,889,129 A | 12/1989 | Dougherty et al. | |
| 4,932,934 A | 6/1990 | Dougherty et al. | |
| 4,968,715 A | 11/1990 | Dougherty et al. | |
| 5,002,962 A | 3/1991 | Pandey et al. | |
| 5,015,463 A | 5/1991 | Dougherty et al. | |
| 5,028,621 A | 7/1991 | Dougherty et al. | |
| 5,093,349 A | 3/1992 | Pandey et al. | |
| 5,145,863 A | 9/1992 | Dougherty et al. | |
| 5,171,741 A | 12/1992 | Dougherty | |
| 5,173,504 A | 12/1992 | Dougherty | |
| 5,190,966 A | 3/1993 | Dougherty et al. | |
| 5,198,460 A | 3/1993 | Pandey et al. | |
| 5,225,433 A | 7/1993 | Dougherty et al. | |
| 5,257,970 A | 11/1993 | Dougherty | |
| 5,314,905 A | 5/1994 | Pandey et al. | |
| 5,438,071 A | 8/1995 | Clauss et al. | |
| 5,459,159 A | 10/1995 | Pandey et al. | |
| 5,498,710 A | 3/1996 | Pandey et al. | |
| 5,506,255 A * | 4/1996 | Smith et al. | ............... 514/410 |
| 5,591,847 A | 1/1997 | Pandey et al. | |
| 5,667,998 A | 9/1997 | Dougherty et al. | |
| 5,686,280 A | 11/1997 | Dougherty et al. | |
| 5,756,541 A | 5/1998 | Strong et al. | |
| 5,770,730 A | 6/1998 | Pandey et al. | |
| 5,864,035 A | 1/1999 | Pandey et al. | |
| 5,906,928 A | 5/1999 | Dougherty et al. | |
| 5,952,366 A | 9/1999 | Pandey et al. | |
| 6,103,751 A | 8/2000 | Pandey et al. | |
| 6,534,040 B1 * | 3/2003 | Pandey et al. | ........... 424/9.362 |

FOREIGN PATENT DOCUMENTS

WO    WO 9313769    7/1993

(Continued)

OTHER PUBLICATIONS

Burns, et al., "Nuclear Imaging in Drug Discovery, Development, and Approval" Birkhauser, 1993.

(Continued)

*Primary Examiner*—Dameron L. Jones
(74) *Attorney, Agent, or Firm*—Michael L. Dunn

(57) ABSTRACT

A method for MR imaging that comprises conducting the MR imaging after injecting compositions that are chemical combination of porphyrins, chlorins, bacteriochlorins, and related tetra-pyrrolic compounds with radioactive elements such as Technetium[99], Gadolinium, Indium[111] and radioactive iodine. When the element can form cations, the compound is usually a chelate with the porphyrin or chlorin structure. When the element forms anions, the compound is usually a direct chemical combination of the radioactive element into the porphyrin or chlorin structure. The method uses the compounds of the invention for diagnostic imaging of hyperproliferative tissue such as tumors and new blood vessel growth as is associated with the wet form of age related macular degeneration and methods of making the compounds. Compounds for MRI contrast imaging of the invention are usually Tc[99], In[111] or Gd(III) complexes of compounds of the formula:

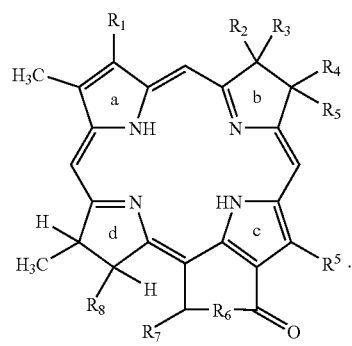

16 Claims, 17 Drawing Sheets

FOREIGN PATENT DOCUMENTS

| | | |
|---|---|---|
| WO | WO 9732885 | 9/1997 |
| WO | WO 9967248 | 12/1999 |
| WO | WO 9967249 | 12/1999 |

OTHER PUBLICATIONS

Dougherty, "Photosensitization of Malignant Tumors", Seminars in Surgical Oncol., 1986, 24-37, 2.

Dougherty, Yearly Review "Photodynamic Therapy", Photochem. Photobiol., 1993, 895-900, 58(6).

Dougherty, Review "Photodynamic Therapy", J. Natl. Cancer Inst., 1998, 889-905, 90(12).

Eckelman, "The Design of Site-Directed Radiopharmaceuticals for use in Drug Discovery", Nuclear Imaging in Drug Discovery, Development and Approval, 1993, 113-134.

Gibson, et al., "The Potential Uses of Radiopharmaceuticals, in the Pharmaceutical Industry", Nuclear Imaging in Drug Discovery, Development and Approval, 1993, 321-331.

Grossman, et al., "Clinical Radioimmunoimaging" Grune & Stratton, Inc., 1988.

Henderson, et al., "An in Vivo Quantitative Structure-Activity Relationship for a Congeneric Series of Pyropheophorbide Derivatives as Photosensitizers for Photodynamic Therapy", Cancer Res., 1997, 4000-4007, 57.

Kessel, et al., "Photosensitization by Synthetic Diporphyrins and Dichlorins in vivo and in vitro", Photochem. Photobiol., 1991, 475-479, 53(4).

Kessel, et al., "Photosensitization with Bacteriochlorins", Photochem. Photobiol., 1993, 200-203, 58(2).

Kozyrev, et al., "Effect of Substituents in $OsO_4$ Reactions of Metallochlorins Regioselective Synthesis of Isobacteriochlorins and Bacteriochlorins", Tetrahedron Lett., 1996, 3781-3784, 37(22).

Li, et al., "Efficient Method for the Synthesis of Bisamino-Ethanethiols and their Pyrrole Conjugates", Heterocycles, 1999, 2849-2854, 51(12).

Li, et al., "Synthesis of $N_2S_2$ Conjugates of Highly Specific Mitochondrial Diazapam Binding Inhibitor (DBI) Receptor Complexes", Heterocycles, 1999, 2855-2860, 51(12).

Mettath, et al., "DNA Interaction and Photocleavage Properties of Porphyrins Containing Cationic Substituents at the Peripheral Position", Bioconjugate Chem., 1999, 94-102, 10.

Pandey, et al., "Structure/Activity Relationships Among Photosensitizers Related to Pheophorbides and Bacteriopheophorbides", Bioorg. Med. Chem. Lett., 1992, 491-496, 2(5).

Pandey, et al., "Alkyl Ether Analogs of Chlorophyll-a, Derivatives:Part 1. Synthesis, Photophysical Properties and Photodynamic Efficacy", Photochem. Photobiol., 1996, 194-204, 64(1).

Pandey, et al., "Comparative in vivo Sensitizing Efficacy of Porphyrin and Chlorin Dimers Joined with Ester, Ether, Carbon-Carbon or Amide Bonds", J. Molecular Recognition, 1996, 118-122, 9.

Pandey, et al., "Chlorin and Porphyrin Derivatives as Potential Photosensitizers in Photodynamic Therapy", Photochem. Photobiol., 1991, 65-72, 53(1).

Pandey, et al., "Shedding Some Light on Tumours", Chem. Indust., 1998, 739-743, 1998.

Pandey, et al., "Synthesis of New Bacteriochlorins and their Antitumor Activity", Bioorganic Med. Chem. Lett., 1994, 1263-1267, 4(10).

Pandey, et al., "Synthesis, Photophysical Properties, in vivo Photosensitizing Efficacy, and Human Serum Albumin Binding Porperties of Some Novel Bacteriochlorins", J. Med. Chem., 1997, 2770-2779, 40.

Sessler, et al., "Texaphyrins: Synthesis and Applications", Acc. Chem. Res., 1994, 43-50, 27.

Wang, et al., "Design and Synthesis of ($^{III}$In)DTPA-Folate for Use as a Tumor-Targeted Radiopharmaceutical", Bioconjugate Chem., 1997, 673-679, 8.

US 6,159,469, 12/2000, Choi et al. (withdrawn)

* cited by examiner

Baseline (left) and 24-hour post-injection images (right) of a tumor-bearing rat. Contrast medium was Magnavist - the standard, commercially-available agent. Tumor area of interest "1" revealed to signal enhancement, visually or quantitatively.

Baseline (left) and 24-hour post-injection images (right) of a tumor-bearing rat. Contrast medium was Gd-HPPH. Area of interest "3" increases markedly, from 623 to 881. The effect is striking both visually as well as quantitatively. Note that the signal enhancement is largely restricted to tumor: fat is unchanged (1998 goes to 1939), and muscle enhancement is minimal.

*In vivo* measurement of tumor (——) vs muscle (----) uptake by *in vivo* reflection spectroscopy in a mouse bearing a RIF tumor.

Reagents: a. Et$_3$N; b. (CH$_2$NH$_2$)$_2$;
c. BH$_3$; d. HCl; e. NaOH;
f. BrCH$_2$CO$_2$Bu$^t$; g. H$_2$,Pd/C

23

$R_3$ = phenyl-$CH_2$-DTPA or $N_2S_2$ conjugates
R = -$(CH_2)$n-DTPA or $N_2S_2$ conjugates
R and $R_1$ = Substituents with variable liphophilicity $R_3$ = phenyl-$CH_2$-DTPA or $N_2S_2$ conjugates
R = -$(CH_2)_n$-DTPA or $N_2S_2$ conjugates
R = Substituents with variable lipophilicity $R_3$ = phenyl-$CH_2$-DTPA or $N_2S_2$ conjugates
$R$ = -$(CH_2)n$-DTPA or $N_2S_2$ conjugates
$R$ and $R_1$ = Substituents with variable liphophilicity $R_3$ = phenyl-$CH_2$-DTPA or $N_2S_2$ conjugates
R = -$(CH_2)$n-DTPA or $N_2S_2$ conjugates
R and $R_1$ = Substituents with variable liphophilicity

METHOD FOR USING CHLORIN AND BACTERIOCHLORIN-BASED AMINOPHENYL DTPA AND $N_2S_2$ CONJUGATES FOR MR CONTRAST MEDIA AND RADIOPHARMACEUTICALS

This application is a continuation-in-part of U.S. patent application Ser. No. 09/739,155 filed Dec. 18, 2000 now U.S. Pat. No. 6,534,040 which in turn claims priority from Provisional Patent Application No. 60/171,961 filed Dec. 23, 1999.

STATEMENT REGARDING FEDERALLY SPONSORED RESEARCH

This invention was made with funding from the National Institute of Health Grant No. R21 CA109914. The United States Government may have certain rights in this invention.

BACKGROUND OF THE INVENTION

Cancer is the second most common cause of death in the United States, accounting for 20% of all deaths. Until now, medicine has tried to overwhelm the cancer cell with brute force, slicing it out with surgery, zapping it with radiation, or poisoning it with chemotherapy. All too often, however, a few cells survive the onslaught and germinate, sometimes years later, into tumors that are impervious to treatment. If tumors can be diagnosed at early stages, it will certainly increase the survival rate of the cancer patients. Therefore, efforts are currently underway in our and various other laboratories to develop efficient tumor diagnostic imaging agents.

For many years, in vivo imaging of human anatomy was dependent upon the intravenous administration of radioactive atoms (nuclear medicine) or non-radioactive iodinated contrast media (various x-ray tests and computed tomography). However, over the last decade magnetic resonance imaging (MRI) has assumed a critical role in imaging, and, unlike x-rays or computed tomography, MR uses contrast media that contain paramagnetic ions, particularly Gadolinium [Gd(III)]. Paramagnetic ions are not themselves "seen" by the MR scanner. Rather, they affect the water in body tissue so as to increase the "signal" emitted by tissue when it is placed in a magnetic field.

By and large, MR contrast media have been neither disease-specific nor organ-specific. Injected intravenously, most are rapidly excreted by the kidneys by glomerular filtration. Although several liver-specific contrast media have been created, other organs have not been successfully targeted, and no tumor-avid MR contrast agents are available to date.

Because of the importance of detection of unknown primary tumor and metastatic disease in diagnostic oncology imaging, a tumor-avid MR contrast medium would have high implications for prognosis, therapy selection, and patient outcomes. The entire issue of cure versus palliation would be impacted.

In recent years several reports focused on certain Gd-based macrocycles as potential magnetic resonance imaging (e.g. Z. D. Grossman and S. F. Rosebrough, Clinical Radioimmunoimaging, *Grune & Stratton Inc.*, 1988) and $^{99m}$Tc or $^{111}$In chelated compounds as radiopharmaceuticals (e.g. H. D. Burns, R. F. Gibson, R. F. Dannals and P. K. S. Siegel (Eds.); Nuclear imaging in Drug Discovery, Development and Approval, *Birkhauser*, 1993, and G. B. Saha, Fundamentals of Nuclear Pharmacy, *Springer-Verlag*, 1992).

Since the approval of $[Gd(DTPA)(H_2O)]^{2-}$ in 1988, more than 30 metric tons of Gadolinium have been administered to millions of patients worldwide. Approximately 30% of MRI exams include contrast agents, and this percentage is projected to increase as new agents and applications appear. Gadolinium is also finding a place in medical research. Over 600 references to Gadolinium appear each year in the basic science literature. While other types of MRI contrast agents, namely an iron-particle-based agent and a manganese (II) chelate have been approved, Gd(III) remains the dominant material. The reasons for this include the direction of MRI development and the nature of Gd chelates. The signal intensity in MRI stems largely from the local value of the longitudinal relaxation rate of water protons, $1/T_1$, and the transverse rate $1/T_2$. Signal tends to increase with increasing $1/T_1$ and decrease with increasing $1/T_2$. Pulse sequences that emphasize changes in $1/T_1$ are referred to as $1/T_1$-weighed, and the opposite is true for $T_2$-weighed scans. Contrast agents increase both $1/T_1$ and $1/T_2$ to varying degrees, depending on their nature as well as the applied magnetic field. Agents such as Gadolinium (III) that increases $1/T_1$ and $1/T_2$ by roughly similar amounts are best visualized using $T_1$-weighted images, because the percentage change in $1/T_1$ in tissue is much greater than that in $1/T_2$. The longitudinal and transverse relaxivity values $r_1$ and $r_2$ refer to the increase in $1/T_1$ and $1/T_2$, respectively, per milliomole of agent. $T_1$ agents usually have $r_2/r_1$ ratios of 1–2, whereas that value for $T_2$ agents, such as iron oxide particles, is as high as 10 or more. Advances in MRI have strongly favored $T_1$ agents and thus Gadolinium (III). Faster scans with higher resolution require more rapid radio frequency pulsing and are thus generally $T_1$-weighed, since the MR signal in each voxel becomes saturated. $T_1$ agents relieve this saturation by restoring a good part of the longitudinal magnetization between pulses. At the same time a good $T_1$ agent would not significantly affect the bulk magnetic susceptibility of the tissue compartment in which it is localized, thus minimizing any inhomogeneities which can lead to image artifacts and/or decreased signal intensity.

The other important and interesting characteristic of Gadolinium (III) chelates is their stability. They remain chelated in the body and are excreted intact. For example, the off-the shelf ligands like DTPA form complexes so stable that while the agent is in vivo, there is no detectable dissociation. Owing to their large size, lanthanides tend to favor high coordination number in aqueous media. Currently, all Gd(III)-based chelates approved for use in MRI are nine-coordinate complexes in which the ligand occupies eight binding sites at the metal center and the ninth coordinate site is occupies by a solvent water molecule.

Radiopharmaceuticals are drugs containing a radionuclide and are used routinely in nuclear medicine department for the diagnosis or therapy. Radiopharmaceuticals can be divided into two primary classes: Those whose biodistribution is determined exclusively by their chemical and physical properties (like iodine-131) and those whose ultimate distribution is determined by their biological interactions (like a radiolabeled antibody). The latter class includes more target-specific radiopharmaceuticals. A target-specific radiopharmaceutical consists of four parts: a targeting molecule, a linker, a chelating ligand and a radionuclide. The targeting molecule serves as the vehicle, which carries the radionucleide to the target site in diseased tissue. The radionuclide is the radiation source.

Metallic radionuclides offer many opportunities for designing new radiopharmaceuticals by modifying the coordination environment around the metal with a variety of chelators. Most of the radiopharmaceuticals used in conventional nuclear medicine are $^{99m}$Tc labeled, because of its short half-life (6 hours) and ideal gamma emission (140 KeV). Millicurie quantities can be delivered without excessive radiation to the patient. The monoenergetic 140-KeV photons are readily collimated, producing images of superior spatial resolution. Furthermore, $^{99m}$TC is readily available in a sterile, pyogen-free, and carrier-free state from $^{99}$MO-$^{99m}$TC generators. Its 6 h half-life is sufficiently long to synthesize the labeled radiopharmaceuticals, assay for purity, inject the patient, and image yet short enough to minimize radiation dose. Another radionuclide successfully used is $^{111}$In. The success of the pharmaceutical IN-DTPA-Octreotide (OCTREOSCAN), used for diagnosis of somatostatin receptor-positive tumors, has intensified the search for new target-specific radiopharmaceuticals. Compared to $^{99m}$Tc, the half-life of $^{111}$In is much longer (72 hours).

Certain porphyrins and related tetrapyrrolic compounds tend to localize in malignant tumors and other hyperproliferative tissue, such as hyperproliferative blood vessels, at much higher concentrations than in normal tissues, so they are useful as a tool for the treatment of various type of cancers and other hyperproliferative tissue by photodynamic therapy (PDT) (T. J. Dougherty, C. J. Gomer, B. W. Henderson, G. Jori, D. Kessel, M. Kprbelik, J. Moan, Q. Peng, *J. Natl. Cancer Inst.*, 1998, 90, 889). However, most of the porphyrin-based photosensitizers including PHOTOFRIN® (approved worldwide for the treatment of tumors) clear slowly from normal tissue, so patients must avoid exposure to sunlight for a significant time after treatment. In recent years, a number of chlorophyll analogs have been synthesized and evaluated for their use as photosensitizers for PDT (e.g. R. K. Pandey, D. Herman, *Chemistry & Industry*, 1998, 739). Among these photosensitizers, the hexyl ether derivative of pyropheophorbide-a 9 (HPPH) (e.g. R. K. Pandey, A. B. Sumlin, S. Constantine, M. Aoudia, W. R. Potter, D. A. Bellnier, B. W. Henderson, M. A. Rodgers, K. M. Smith and T. J. Dougherty, *Photochem. Photobiol.*, 1996, 64, 194; B. W. Henderson, D. A. Bellnier, W. R. Graco, A. Sharma, R. K. Pandey, L. A. Vaughan, W. R. Weishaupt and T. J. Dougherty, *Cancer Res.*, 1997, 57, 4000; and R. K. Pandey, T. J. Dougherty, U.S. Pat. No. 5,198,460; 1993, U.S. Pat. No. 5,314,905, 1994 and U.S. Pat. No. 5,459,159, 1995) and the hexyl-ether derivative of purpurin-18-N-hexylimide 10 (e.g. R. K. Pandey, W. R. Potter and T. J. Dougherty, U.S. Pat. No. 5,952,366, 1999) have shown high tumor uptake and minimal skin phototoxicity compared with PHOTOFRIN®. HPPH is currently in phase I/II clinical trials for treatment of various types of cancer by photodynamic therapy at the Roswell Park Cancer Institute, Buffalo, N.Y. and the results are promising.

BRIEF DESCRIPTION OF THE INVENTION

Figure 1:
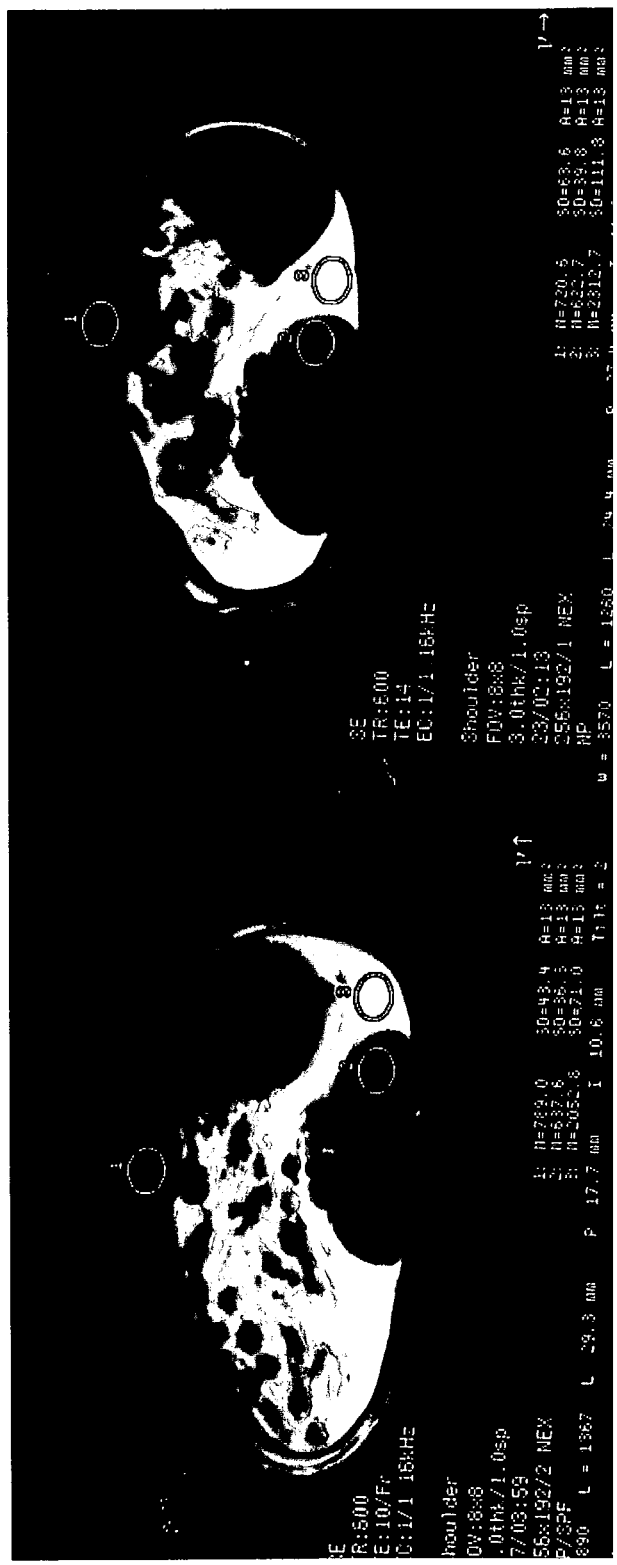
FIG. 1 shows an MR image control using a commercially available contrast agent vs. no use of contrast enhancement agent. The tumor area of the images shows little or no enhancement using the commercially available contrast agent.

The invention includes compositions that are chemical combination of porphyrins and chlorins and related tetrapyrrolic compounds with radioactive elements such as Technetium$^{99}$, Gadolinium, Indium$^{111}$ and radioactive iodine. When the element can form cations, the compound is usually a chelate with the porphyrin or chlorin structure. When the element forms anions, the compound is usually a direct chemical combination of the radioactive element into the porphyrin or chlorin structure.

Examples of porphyrin and chlorin structures that can form compounds with radioactive elements, when modified in accordance with the present invention, are for example described in U.S. Pat. Nos. 5,756,541; 5,028,621; 4,866, 168; 4,649,151; 5,438,071; 5,198,460; 5,002,962; 5,093,349; 5,171,741; 5,173,504; 4,968,715; 5,314,905; 5,459,159; 5,770,730; 5,864,035; 5,190,966; and 5,952,366.

The invention further includes the method of using the compounds of the invention for diagnostic imaging of hyperproliferative tissue such as tumors and new blood vessel growth as is associated with the wet form of age related macular degeneration.

Unexpectedly, porphyrins and chlorins, as above described, upon injection, carry the radioactive element into cells of hyperproliferative tissue and dramatically enhance the signal produced by tumor tissue in MR imaging.

It is to be understood that porphyrin and chlorin compounds (including bacteriochlorins) may be chemically altered to other forms by substitutions and modifications; provided that, the base tetrapyrrolic structure that allows selective entry and retention in hyperproliferative tissue cells (e.g. tumors) is retained.

Compounds of the invention usually have the formula

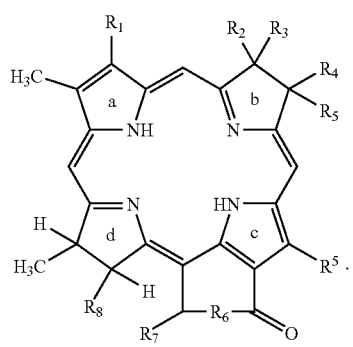

In the above formula,

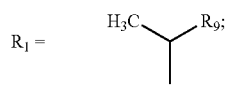

$(CH_2)_2CONHphenylene\ CH_2DTPA$

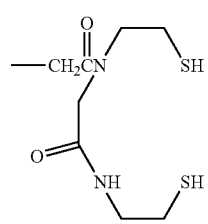

or

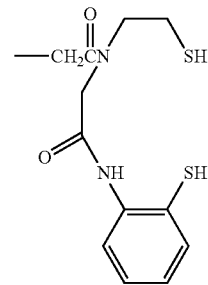

where $R_9$=—$OR_{10}$ where $R_{10}$ is lower alkyl of 1 though 6 carbon atoms; $R_2$ is —$CH_3$, $R_5$ is —$CH_2CH_3$, and $R_3$ and $R_4$ together form a covalent bend or $R_2$ and $R_3$ together are=O, $R_4$ is —$CH_2CH_3$ and $R_5$ is —$CH_3$; $R_6$ is —$N(R_{11})$— or a covalent bond; $R_7$ is =O when $R_6$ is —$N(R_{11})$— and $R_7$ is H when $R_6$ is covalent bond; and $R_8$ is —$(CH_2)CO_2CH_3$, —$(CH_2)_2CONHphenyleneCH_2DTPA$,

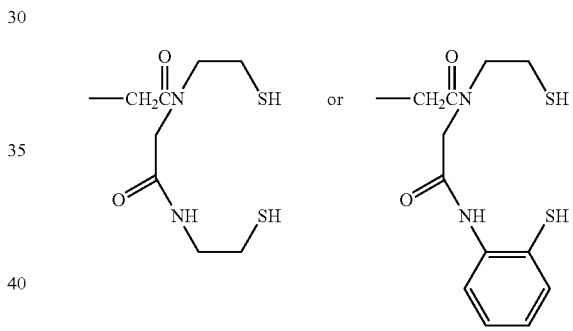

$R_{11}$ is lower alkyl of 1 through 6 carbon atoms, —$(CH_2)_2CONHphenyleneCH_2DTPA$,

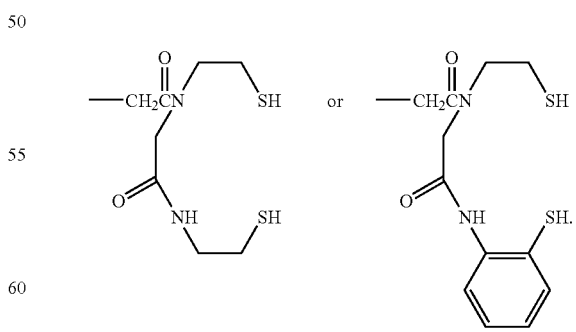

provided that only one of $R_1$, $R_8$ or $R_{11}$ is —$(CH_2)_2CONHphenyleneCH_2DTPA$,

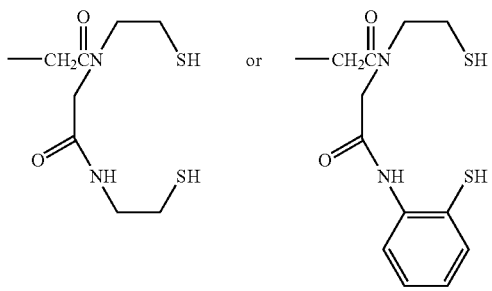

DETAILED DESCRIPTION OF THE INVENTION

An objective of the invention was to use these photosensitizers as a vehicle for delivering the desired conjugate (chelated with Gd or radionuclides) to tumor. The chelate is "bifunctional" because, it binds the Gd at one end and binds the target specific vehicle at the other. The chelate is a multidentate ligand, which has appropriate ligating groups for coordination to the metal. In a preferred embodiment, our invention includes:

Development of chlorin and bacteriochlorin-based Gd(III)aminophenyl DTPA conjugates with variable lipophilicity as tumor diagnostic agent by MRI.

Development of chlorin and bacteriochlorin-based $^{111}$In aminophenyl DTPA and $^{99m}$Tc $N_2S_2$ conjugates with variable lipophilicity as tumor diagnostic radiopharmaceuticals.

A goal has been: (i) to successfully bind Gadolinium to a tumor-avid porphyrin, originally designed for photodynamic therapy (PDT), and to prove that striking tumor uptake at 24 hours enhances the "signal" produced by tumor, thus dramatically increasing its conspicuity on MR imaging and (ii) to prepare related $^{99m}$Tc and $^{111}$In labeled radiopharmaceuticals as diagnostic agents for nuclear medicine.

This invention includes the synthesis and application of certain chlorin and bacteriochlorin-based bisaminoethanethiol ($N_2S_2$) and modified ditetratriethylamine penta carboxylic acid (DTPA) conjugates as MR contrast media and radiopharmaceuticals for diagnosis of primary malignancy and metastatic disease.

Figure 4:
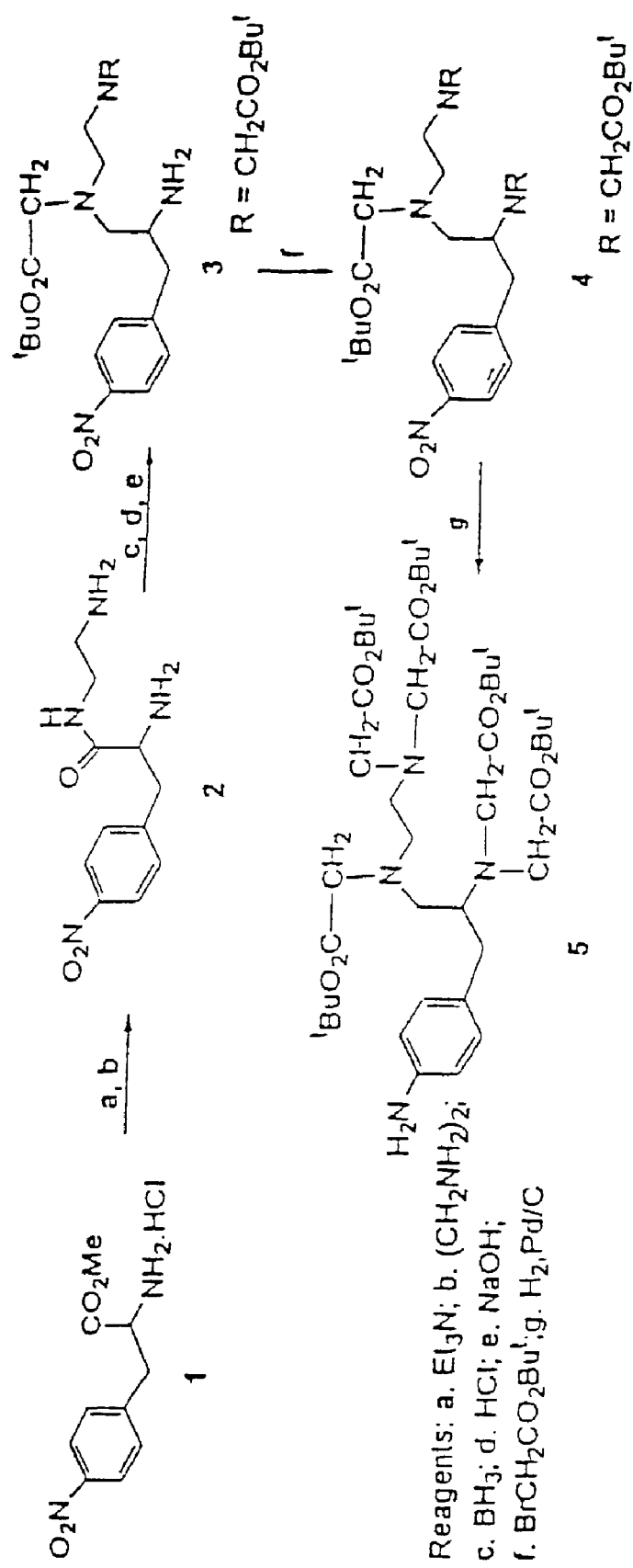
FIG. 4 is a schematic diagram showing chemical synthesis of 4-aminophenyl DTPA penta-tert-butyl esters.
Figure 5:
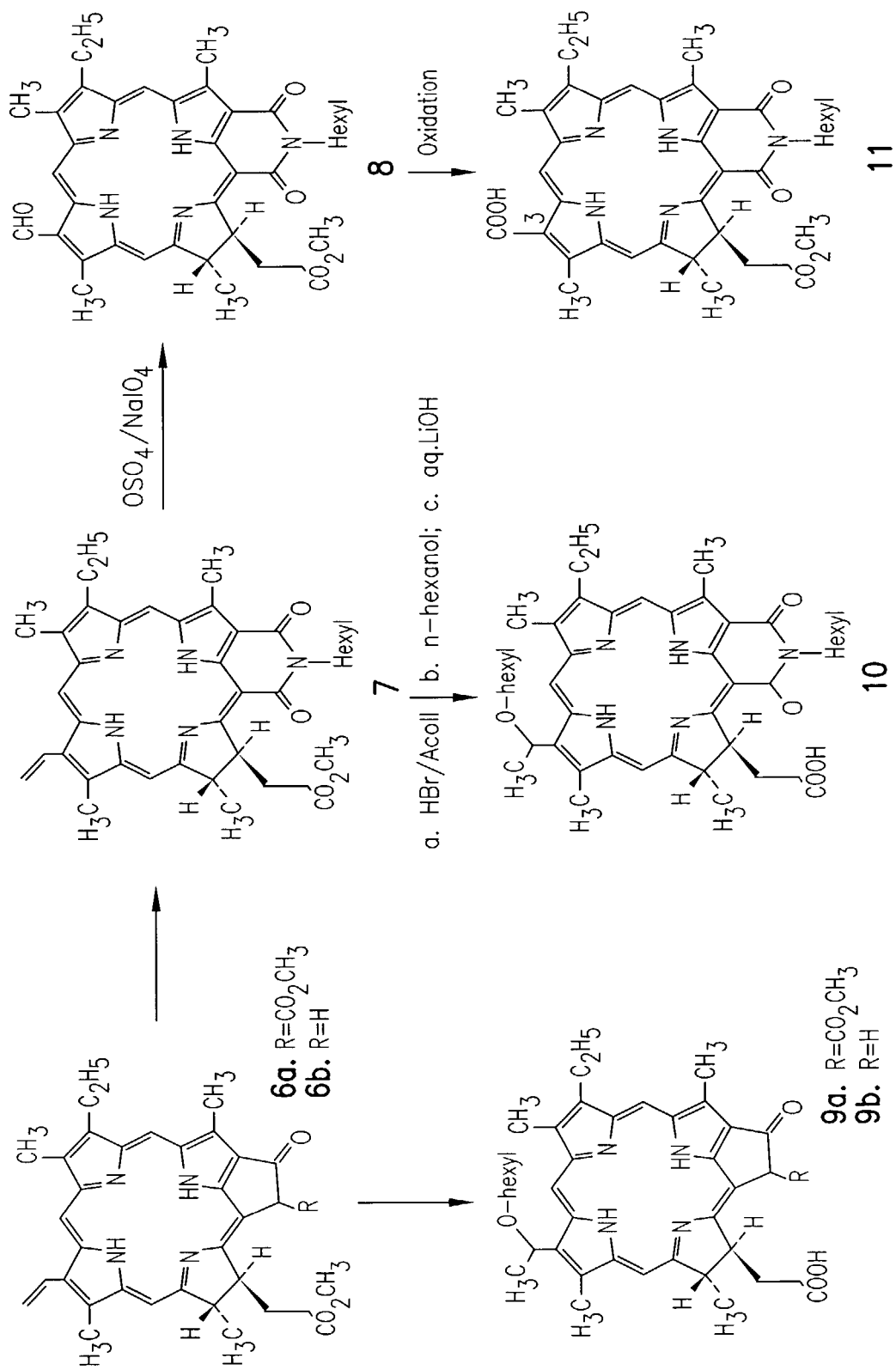
FIG. 5 is a schematic diagram showing chemical synthesis of carboxy 3-(hexyloxy)ethyl pyropheophorbide-a from methylpheophorbide-a.
Figure 6:
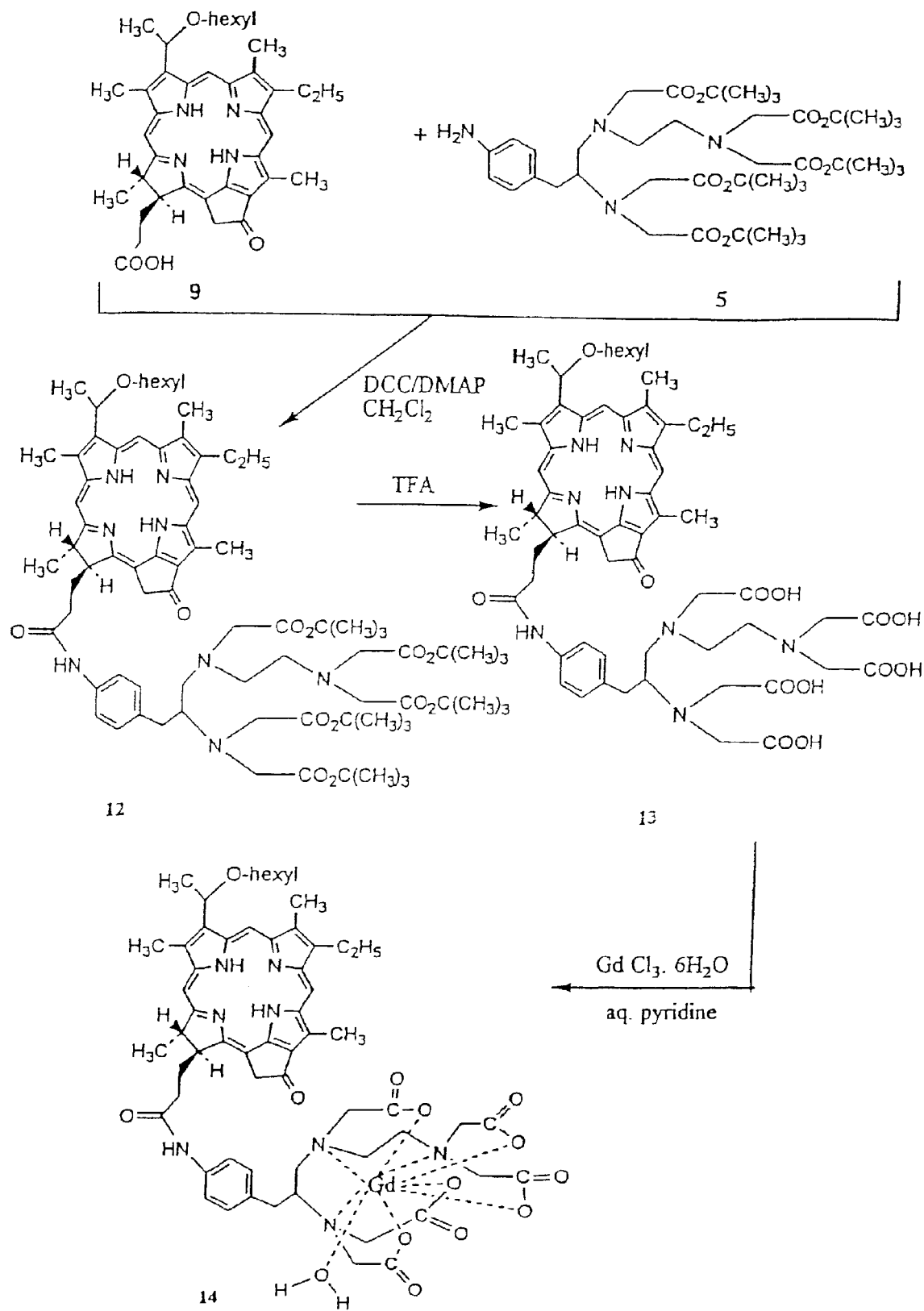
FIG. 6 is a schematic diagram showing chemical synthesis of HPPH-aminophenyl DTPA from carboxy 3-(hexyloxy)ethyl pyropheophorbide-a and 4-aminophenyl DTPA penta-tert-butyl ester followed by reaction with Gadolinium (III) trichloride to form HPPH-aminophenyl DTPA.

The following examples describe examples for synthesis and use of magnetic resonance imaging agents. Synthesis of HPPH-Gd(III)aminophenylDTPA 14: For the preparation of the title compound, pyropheophorbide-a 6b was obtained from methylpheophorbide-a 6a (which in turn was extracted from *Spirulina Algae*) by following the literature procedure. It was then converted into methyl 3-(hexyloxy)ethyl analog 9a by following a methodology developed in our laboratory. Hydrolysis of the methyl ester functionality with aqueous LiOH/methanol/THF produced the corresponding carboxylic acid 9b in quantitative yield. The reaction of 9b with 4-aminophenyl DTPA penta-tert-butyl esters prepared by following the methodology in FIG. 4 via the carbodiimide approach (R. K. Pandey, F.-Y. Shiau, A. B. Sumlin, T. J. Dougherty and K. M. Smith, *Bioorg. Med. Chem. Lett.*, 1994, 4, 1263) produced the corresponding analog 12 in 57% yield (FIGS. 5 and 6). The structure was confirmed by NMR and mass spectrometry analyses.

Before preparing the Gd(III) complex, the tert-butyl groups in conjugate were converted into corresponding carboxylic acid by reacting with trifluoroacetic acid (yield 100%). For the preparation of Gd(III) complex 14, the conjugate was dissolved in pyridine and Gadolinium chloride hexahydrate dissolved in deionized water. The mixture was stirred at room temperature for 2 h. After the completion of the reaction (monitored by TLC), pyridine was removed under high vacuum. The residue was washed with water to remove the excess of Gadolinium chloride, dried under vacuum and the title compound was isolated in 92% yield. The structure of the final product was confirmed by mass spectrometry.

Figure 7:
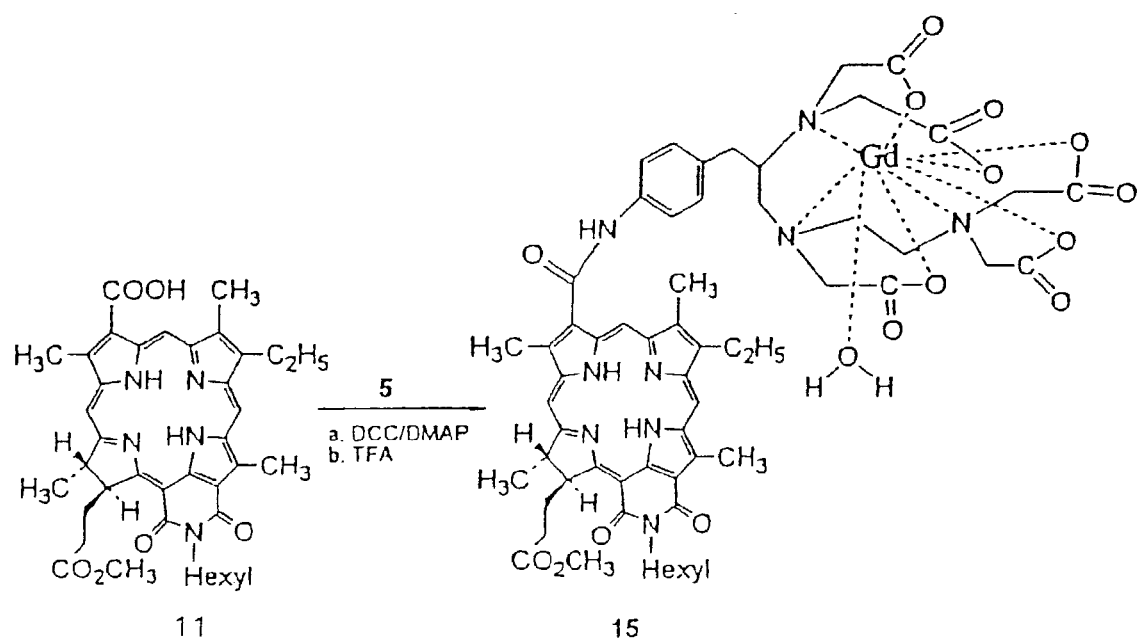
FIG. 7 is a schematic diagram showing chemical synthesis of purpurin-18-imide-Gd(III) aminophenyl DTPA (16).
Figure 8:
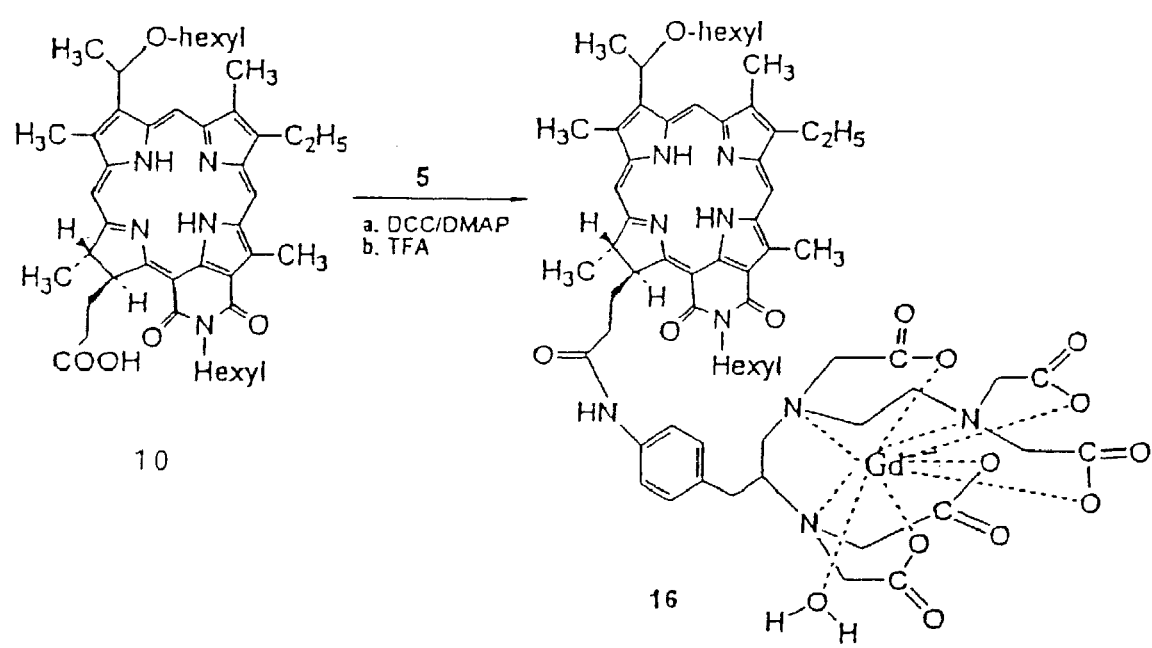
FIG. 8 is a schematic diagram showing preparation of Gd(III) aminophenyl DTPA complex from purpurin 7.

Synthesis of Purpurin-18-imide-Gd(III)aminophenylDTPA 16: Methylpheophorbide-a 7a was converted into the hexylether derivative of N-hexyl purpurinimide in 70% yield. The methyl ester group was then hydrolyzed to the corresponding carboxylic acid 10 by following the methodology as discussed for the preparation of 9b. Purpurin-imide 10 was then reacted with aminophenylDTPA penta tert-butyl ester 5 by following a reaction sequence depicted in FIG. 7 and the intermediate conjugate was isolated in 45% yield. Further reaction with trifluoroaceticacid and then with $GdCl_3.6H_2O$ produced the Gd(III) complex 16 in >90% yield. The structures of the conjugates were confirmed by NMR and mass spectrometry.

In our attempt to investigate the effect of the position of the Gd(III) conjugate in the macrocycle, purpurin-imide 7 was converted into the related carboxylic acid analog 11 by conventional procedures. Reaction of 10 with aminophenyl DTPA 5 will produce Gd(III) aminophenyl DTPA conjugate 15, purpurin 18-3-devinyl-3[4'-amidophenyl Gadolinium (III) DTPA]-N-hexylimide.

In this series of compounds, the overall lipophilicity of the molecule can be altered by varying the length of the carbon chain of either the alkyl ether substituents and/or N-substituted alkyl chain. Thus, these compounds provide a unique opportunity to investigate the correlation of tumor uptake and lipophilicity.

Figure 3:
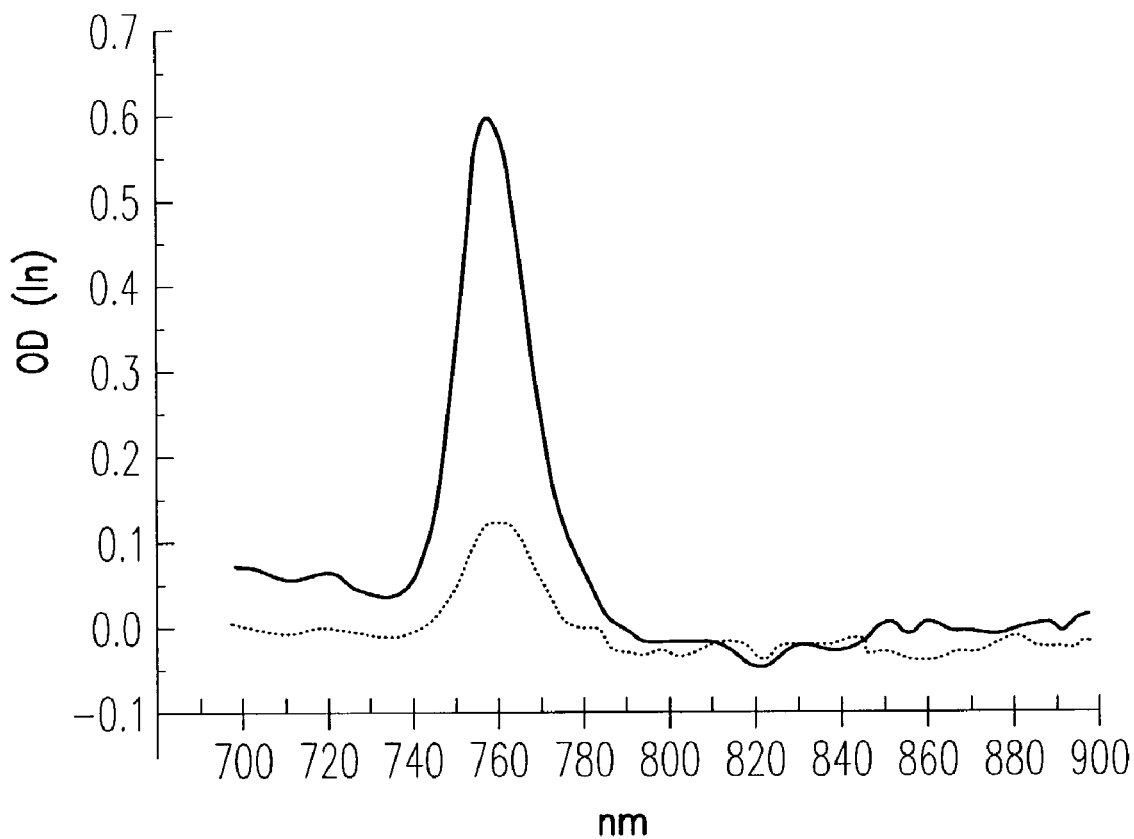
FIG. 3 is a graph of in vivo measurement of tumor vs. muscle uptake by reflection spectroscopy of the compound shown in FIG. 3.
Figure 3A:
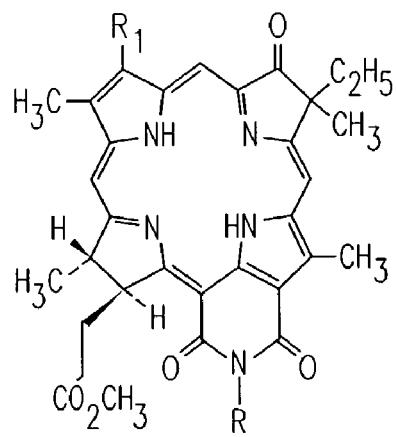
Figure 9:
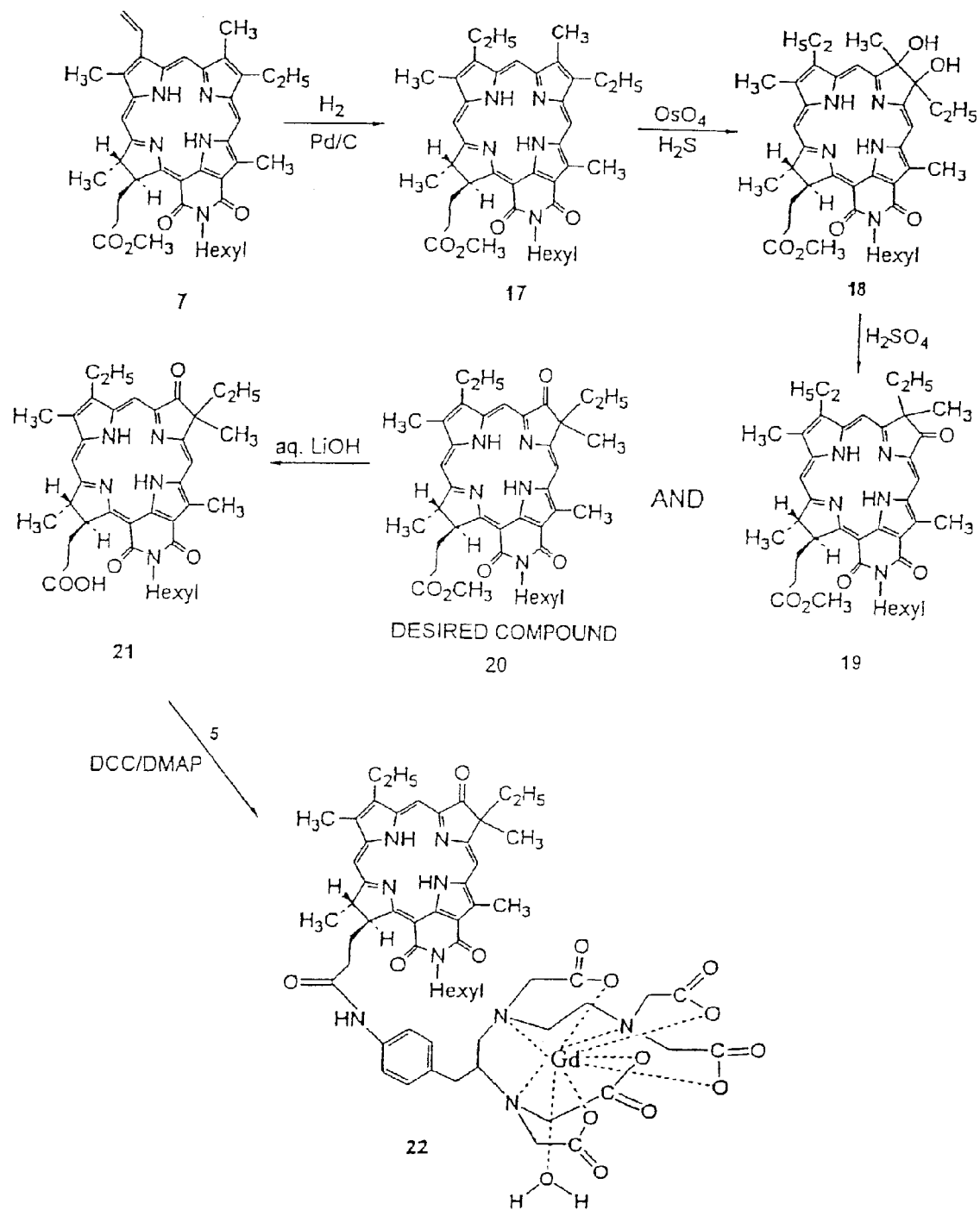
FIG. 9 is schematic diagram showing preparation of bacteriochlorin based Gd(III) aminophenyl DTPA.
Figure 10:
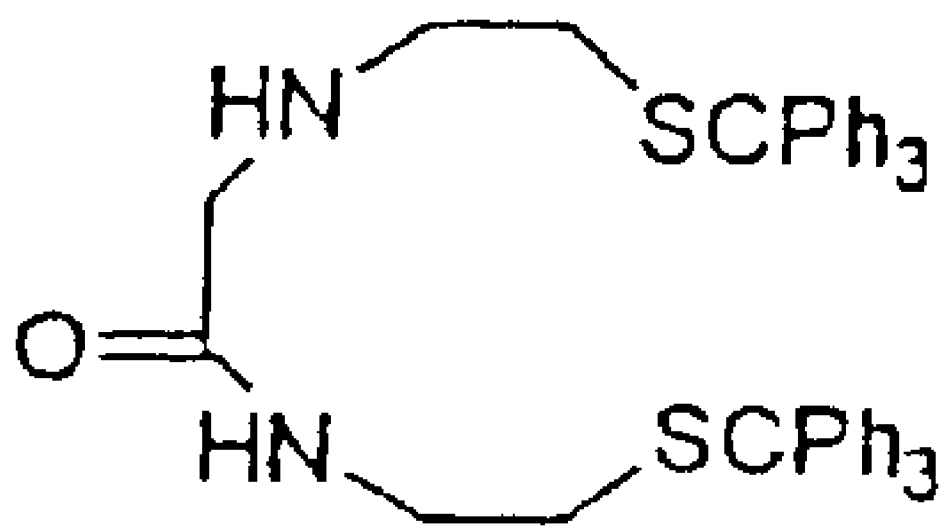
FIG. 10 is a schematic formula for bisaminoethanethiol compound 23.
Figure 11:
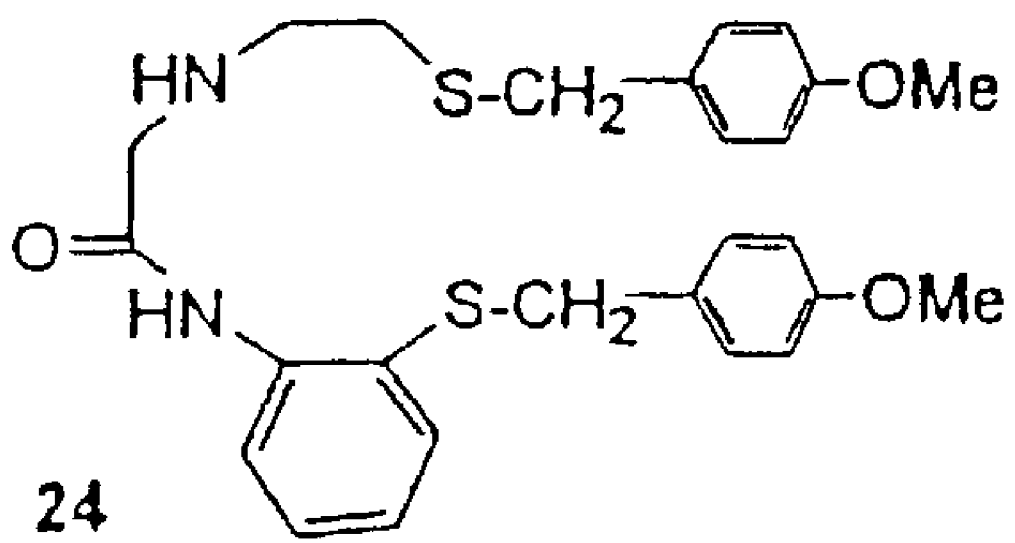
FIG. 11 is a schematic formula for bisaminoethanethiol compound 24.
Figure 12:
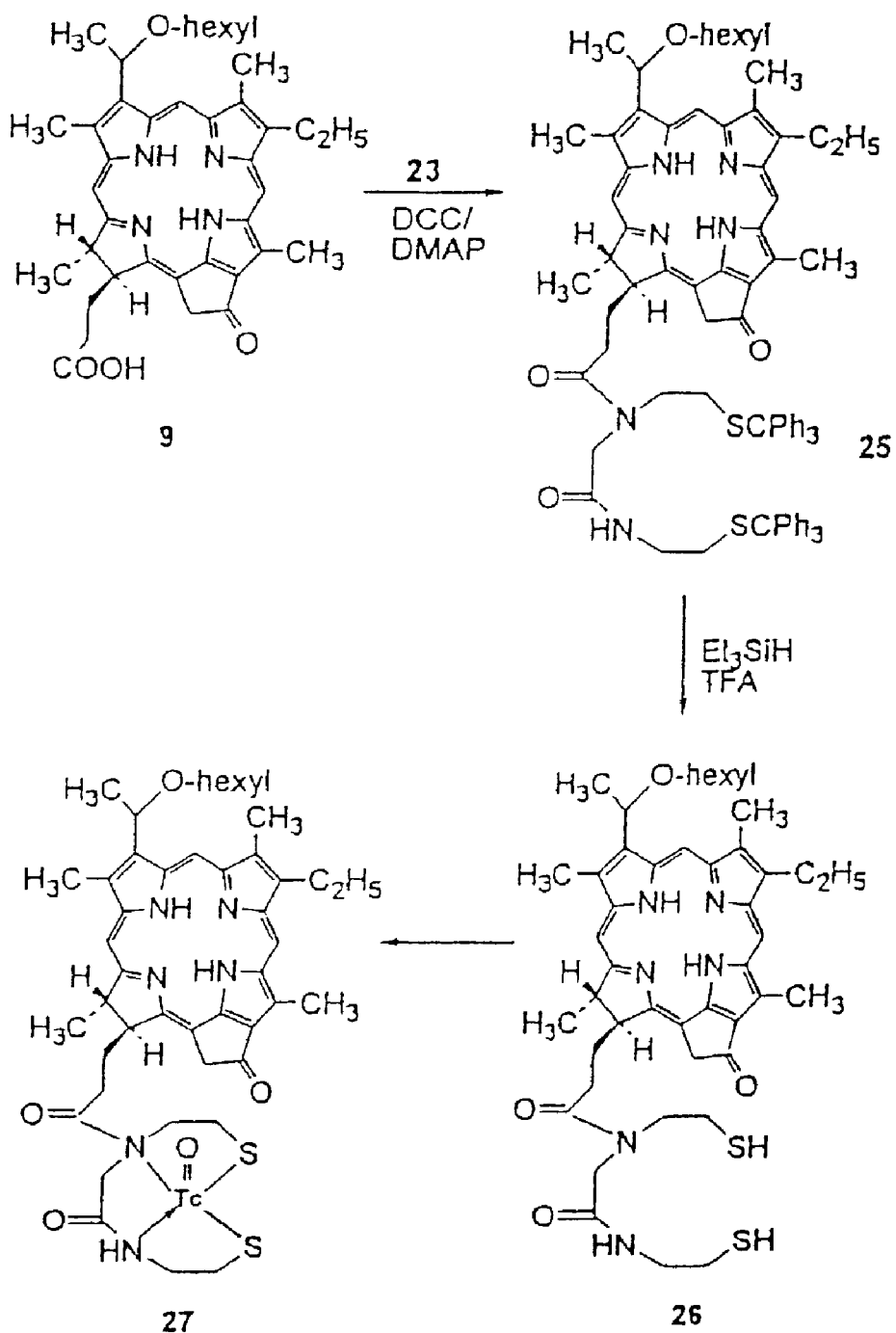
FIG. 12 is a schematic diagram showing preparation of HPPH based bisaminoethanethiol conjugate 27.
Figure 13:
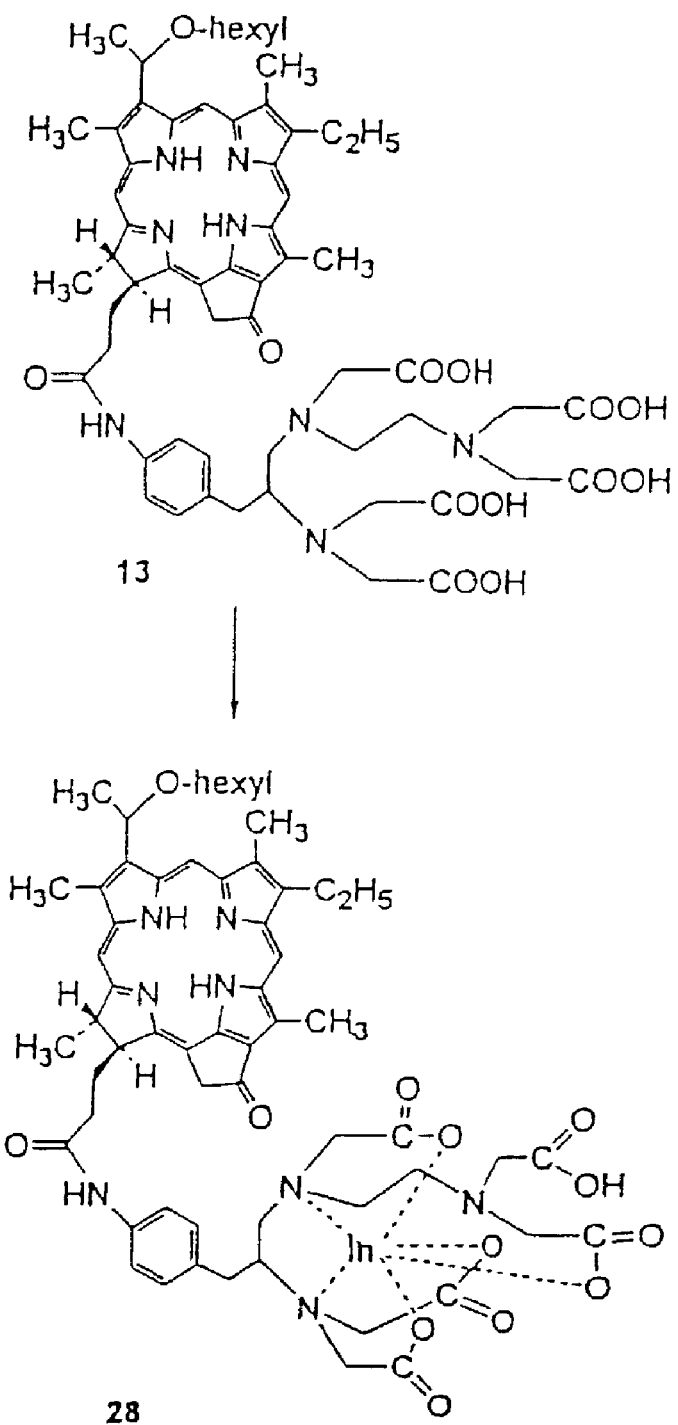
FIG. 13 is a schematic diagram showing preparation of HPPH based In Aminophenyl DTPA conjugate 28.
Figure 14:
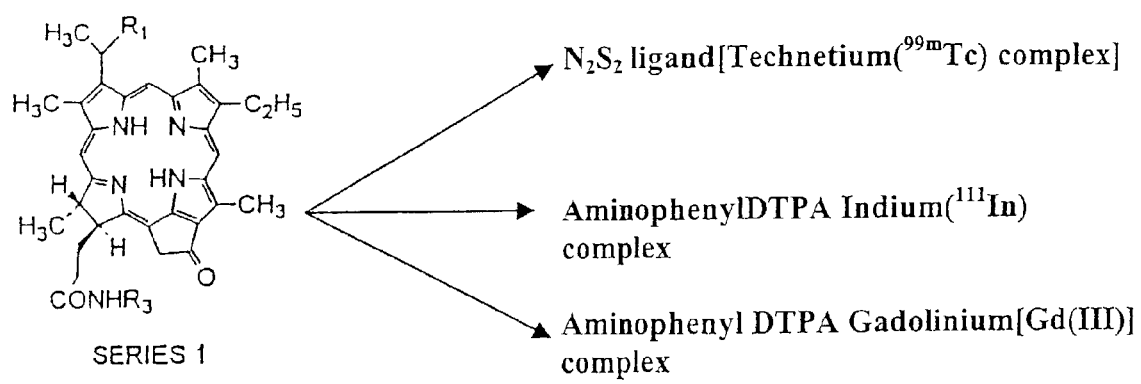
FIG. 14 is a schematic diagram showing preparation of $N_2S_2$ ligand $^{99m}$Tc complex, Aminophenyl DTPA $^{111}$In complex and Aminophenyl DTPA Gd(III) complex, e.g. 3-devinyl-3-(1'-alkoxy ethyl)-17-[3'-(4"-amidobenzyl gadolinium (III)DTPA)]ethyl pyropheophorbide-a, from a DTPA or $N_2S_2$ dihydro tetrapyrrole compound of the invention.
Figure 15:
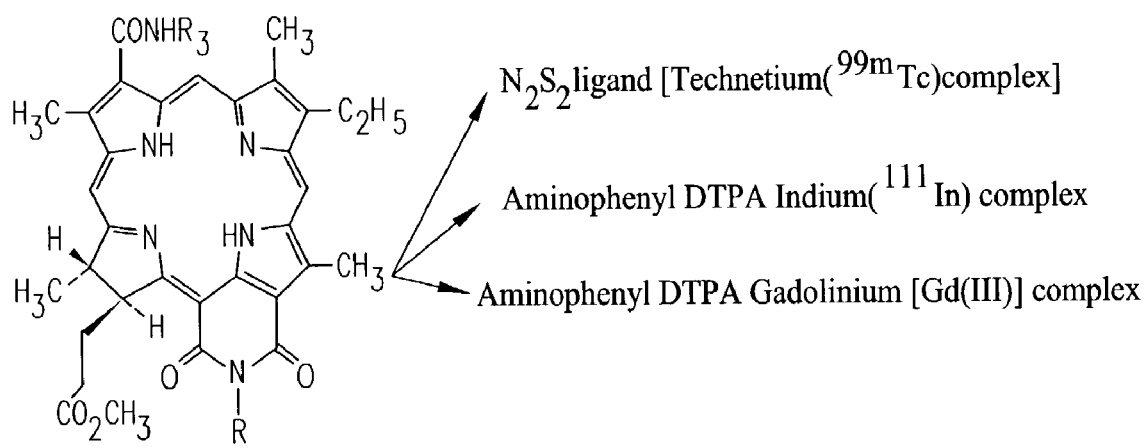
FIG. 15 is a schematic diagram showing $N_2S_2$ ligand $^{99m}$Tc complex, Aminophenyl DTPA "In complex, and Aminophenyl DTPA" $^{111}$In Complex, and Aminophenyl DTPA Gd(III) complex, e.g. purpurin-18-(3-devinyl-[3-(4"-amidobenzyl gadoliniumDTPA)]-N-substituted imide, from a DTPA or $N_2S_2$ dihydro tetrapyrrole compound of the invention.
Figure 16:
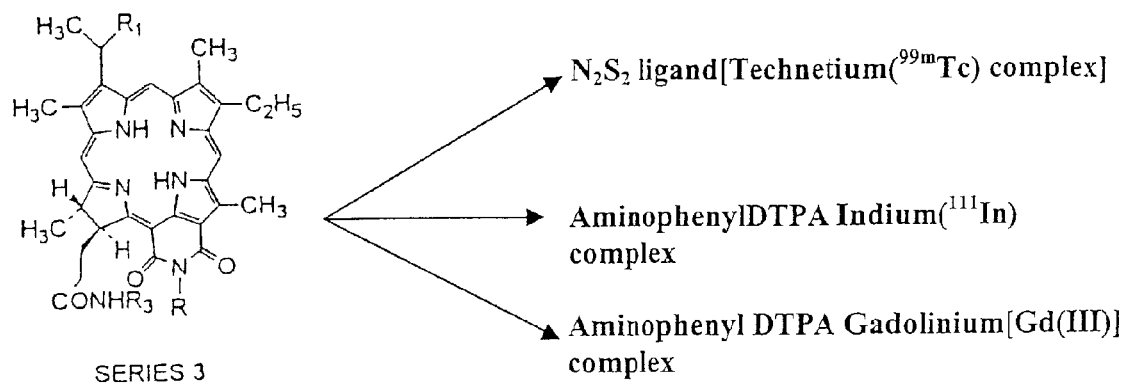
FIG. 16 is a schematic diagram showing $N_2S_2$ ligand $^{99m}$Tc complex, Aminophenyl DTPA "In complex, and Aminophenyl DTPA" $^{111}$In Complex, and Aminophenyl DTPA Gd(III) complex, e.g. purpurin-18-(3-devinyl-3-(1'alkoxy ethyl)-17-[3'-(4"-amidobenzyl gadolinium(III)DTPA)]ethyl pyropheophorbide-a, from a DTPA or $N_2S_2$ dihydro tetrapyrrole compound of the invention.
Figure 17:
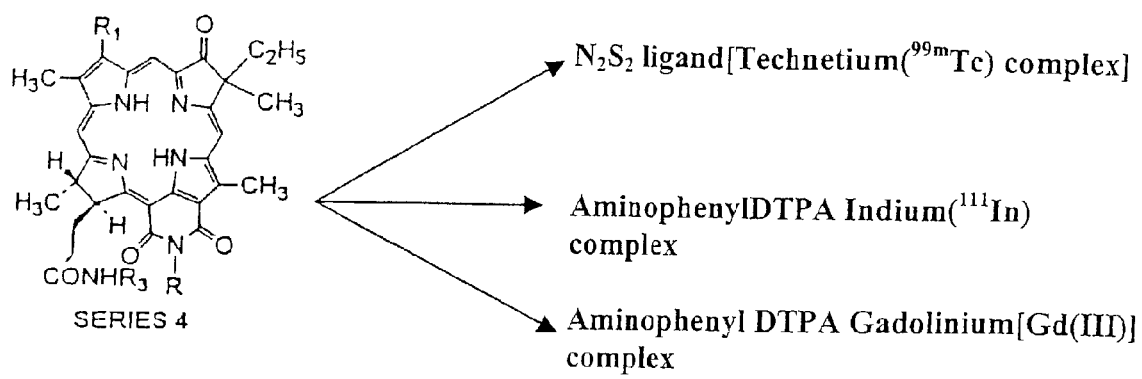
FIG. 17 is a schematic diagram showing $N_2S_2$ ligand $^{99m}$Tc complex, Aminophenyl DTPA "In complex, and Aminophenyl DTPA" $^{111}$In Complex, and Aminophenyl DTPA Gd(III) complex, e.g. bacteriopurpurin 18-3-(alkyl or alkoxyalkyl)-7-keto-17-[3'-(4"-amidobenzyl gadolinium (III)DTPA)]-N-substituted imide, from a DTPA or $N_2S_2$ tetrahydro tetrapyrrole compound of the invention.

Synthesis of Bacteriochlorin BasedGD(III)aminophenylDTPA 22:

Bacteriochlorins are a class of tetrapyrroles in which the two pyrrole units diagonal to each other are reduced. Starting from N-hexyl-purpurin imide 7 we have prepared ketobacteriochlorin 20 by following a reaction sequence illustrated in FIG. 9. In our approach purpurinimide 7 containing a vinyl group at position 3 was converted into the 3-devinyl-3-ethyl analog 17 (also be named as meso-N-hexyl-purpurin-18-imide) by reacting with hydrogen using Pd/C as a catalyst. It was then reacted with osmiumtetroxide/pyridine/ $H_2S$ (A. N. Kozyrev. T. J. Dougherty and R. K. Pandey, *Tetrahedron Lett.*, 1996, 37, 3781) and the corresponding vic-dihydroxybacteriochlorin 18 was isolated in 75% yield as a mixture of diasteriomers (cis-hydroxy groups up or down relative to trans-reduced ring D). The dihydroxy analog as a diasteriomeric mixture was treated with sulfuric acid under pinacol-pinacolone reaction conditions, (R. K. Pandey, T. Tsuchida, S. Constantine, G. Zheng, C. Medforth, A Kozyrev, A. Mohammad, M. A. J. Rodgers, K. M. Smith and T. J. Dougherty, *J. Med. Chem.*, 1997, 40, 2770) and the ketobacteriochlorin, containing keto-group either at 7-(compound 20) or 8-position (compound 19) respectively were isolated in 70% yield. Among these bacteriochlorins, the 7-keto analog 20 showed high tumor uptake as determined by in vivo reflectance spectroscopy in mice model transplanted with RIF tumor (see FIG. 3). The structures of bacteriochlorins 19 and 20 were confirmed by NMR and mass spectrometry analyses.

Our next step was to hydrolyze the methyl ester group in purpurinimide 20 into carboxylic acid 21 before converting it into the corresponding 4-aminophenylDTPA conjugate 22 by following the methodology discussed previously for the preparation of related HPPH and purpurin-imide analogs.

Synthesis of HPPH-based Bisaminoethanethiol conjugates 27: For preparing the $^{99m}$Tc labeled radiopharmaceuticals, two aminobisethanethiols 23 and 24 were prepared by following the methodology developed in our laboratory (G. Li, Q. Ma, B. Ma, Z. D. Grossman and R. K. Pandey, Heterocyclics, 1999, in press; and G. Li, B. Ma, J. R. Missert, Z. D. Grossman and R. K. Pandey, Heterocyclics, in press). For the synthesis of $N_2S_2$ conjugate 26, HPPH was reacted with $N_2S_2$ chelate 23 and the thioprotected HPPH conjugate 25 was isolated in 40% yield. Subsequent deprotection of the thiols with triethysilane/TFA afforded the corresponding bis-aminoethanethiol 26 in quantitative yield. The structure of the newly synthesized compound was confirmed by NMR and mass spectrometry analyses.

The Tc-99m complex 27 was prepared by ligand-exchange reaction with $^{99m}$Tc pertechnatate reduced by Sn(II) glucoheptonate by following the methodology of Kung and coworkers (S. K. Meegalla, K. Plossl, M-P. Kung, S. Chumpradit, D. A. Stevenson, S. A. Kushner, W. T. McElgin, P. D. Mozley and H. F. Kung. J. Med. Chem., 1997, 40, 9). The radiolabeling yield was >80%. The purity of the Tc-99m complex was >95%, by chromatography.

Syntheses of HPPH based $^{111}$In AminophenylDTPA conjugate 28: For the preparation of the title compound, the HPPH-aminophenylDTPA 13 was reacted with $^{111}$In(III) chloride, following the methodology reported by Low and coworkers (S. Wang J. Juo, D. A. Lantrip, D. A. Waters, C. J. Mathias, W. A. Green, P. L. Fuchs and P. S. Low, Bioconjugate Chem., 1997, 8, 673) for the preparation of $^{111}$In DTPA-Folate and the $^{111}$In labeled compound was obtained in 82% yield.

Body Tumor MR Imaging:

HPPH-Gd(III)AminophenylDTPA Conjugate 14:

Following the synthesis of GD-labeled HPPH, a series of three rats were injected intravenously and studied immediately after injection, at 1 hour, and at 24 hours, to establish whether the Gd-HPPH remained in the circulation longer than the current standard contrast medium (Magnavist or Gd-DTPA).

Figure 2:
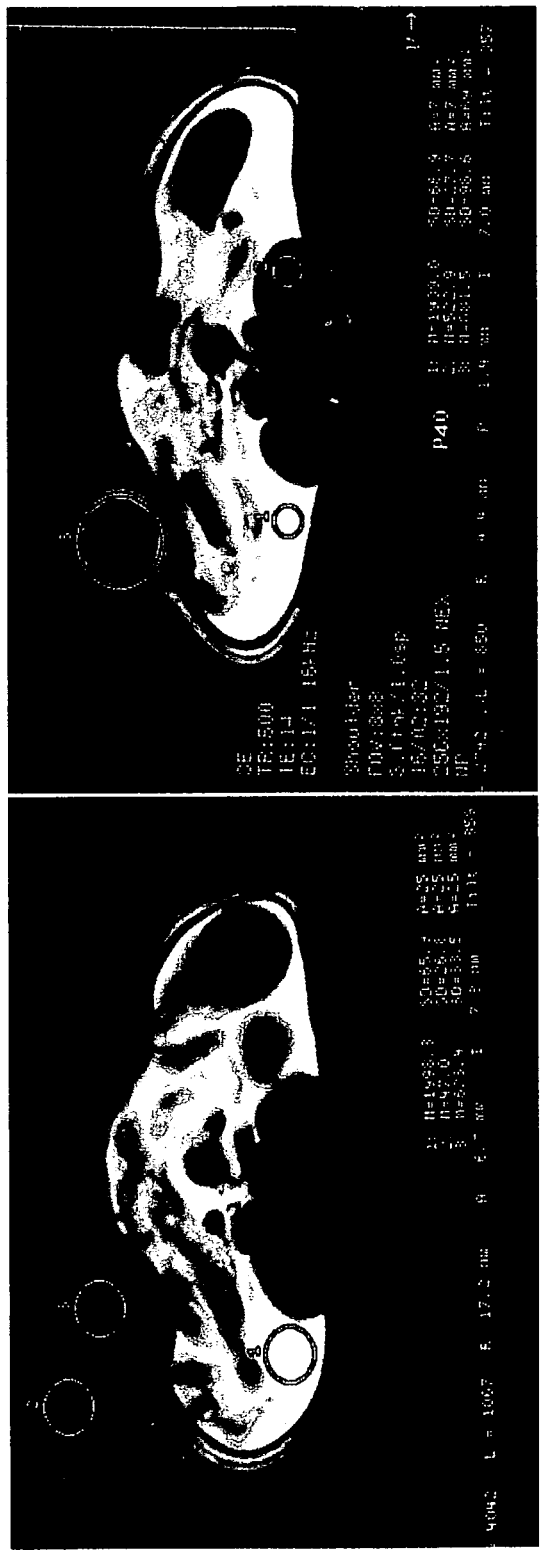
FIG. 2 shows the MR image using a Gd-HPPH contrast agent of the invention vs. no contrast agent. The image formed using the contrast agent of the invention shows dramatic image enhancement of the tumor area.

Whereas Magnavist clears rapidly from the mammalian circulation by glomerular filtration, with a circulatory half-time of 16–20 minutes, the newly-synthesized contrast medium Gd-HPPH, was evident in the cerebral circulation at 1 hour. Subsequently, to establish whether the GD-HPPH is tumor-avid, a single rat with a subcutaneously-implanted Ward colon carcinoma was imaged, 24 hours after intravenous GD-HPPH, A second tumor-bearing rat was imaged 24 hours after injection of Magnavist (See FIGS. 1 and 2). Clearly, the enhanced tumor signal after Gd-HPPH injection indicated that GD-HPPH 14 has potential as a contrast medium for MR. HPPH (a chlorophyll—a derivative) represents the vehicle by which the Gd complex is carried into the tumor. Addition of the Gd chelate to HPPH does not hinder its ability to form singlet oxygen producing efficacy, so this contrast medium also has the potential for dual action: enhanced localization on MR imaging (diagnosis), followed by directed light exposure with tumor injury (treatment). Also, because of its excellent tumor selectivity and high fluorescence, the newly synthesized conjugate can be used for IR imaging. Also, Indium or other radionuclides like Tc-99m (the latter conjugated by an $N_2S_2$ ligand) bound to chlorins and bacteriochlorins synthesized and proposed in this invention have potential as imaging agents for nuclear medicine.

The quantity of material injected usually varies from about 5 to about 20 μmol/kg of body weight and the time to MR imaging from injection is usually from immediately after injection to about 24 hours after injection. A preferred time period for MR imaging after injection is about one hour. Subsequent to intravenous injection, a tumor may be exposed to light at the absorption frequency of the compound at sufficient intensity to cause necrosis of the tumor.

What is claimed is:

1. A method for in vivo MR imaging by intravenous injection of a compound of the formula

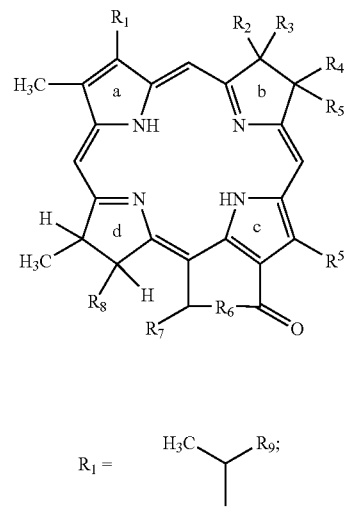

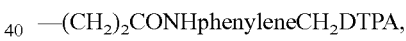

—(CH$_2$)$_2$CONHphenyleneCH$_2$DTPA,

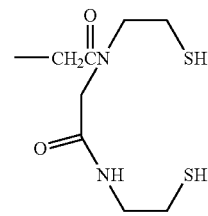

or

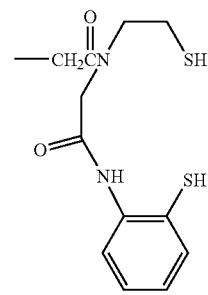

where $R_9$=—$OR_{10}$ where $R_{10}$ is lower alkyl of 1 though 6 carbon atoms; $R_2$ is —$CH_3$, $R_5$ is —$CH_2CH_3$, and $R_3$ and $R_4$ together form a covalent bond or $R_2$ and $R_3$ together are =O, $R_4$ is —$CH_2CH_3$ and $R_5$ is —$CH_3$; $R_6$ is —$N(R_{11})$— or a covalent bond; $R_7$ is =O when $R_6$ is —$N(R_{11})$— and $R_7$ is H when $R_6$ is a covalent bond; and $R_8$ is —($CH_2$)$CO_2CH_3$, —($CH_2$)$_2$CONHphenyleneCH$_2$DTPA,

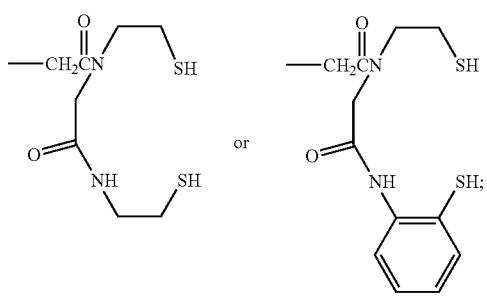

$R_{11}$ is lower alkyl of 1 through 6 carbon atoms —($CH_2$)$_2$CONHphenyleneCH$_2$DTPA,

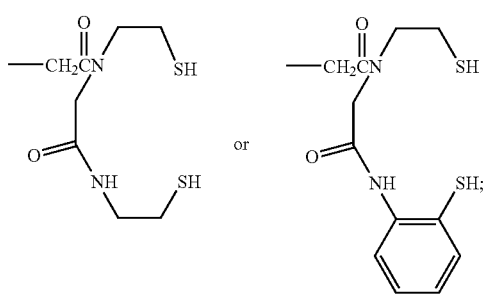

provided that only one of $R_1$, $R_8$ or $R_{11}$ is —($CH_2$)$_2$CONHphenyleneCH$_2$DTPA,

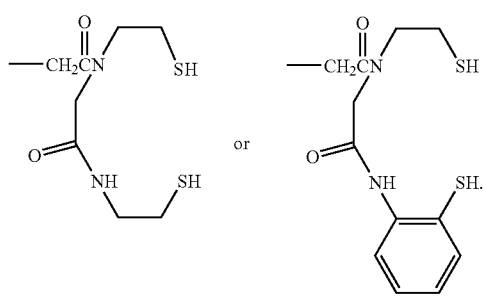

2. The method of claim 1 where $R_1$, $R_8$ or $R_{11}$ is

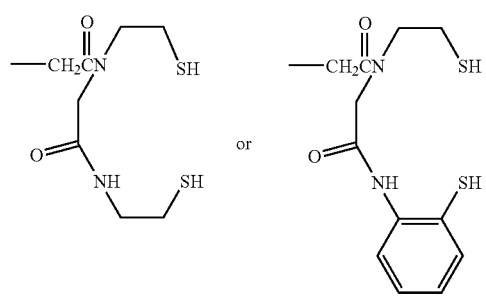

followed by MR imaging.

3. The method of claim 1 where $R_1$, $R_8$ or $R_{11}$ is —($CH_2$)$_2$CONHphenyleneCH$_2$DTPA.

4. The method of claim 2 where $R_8$ is

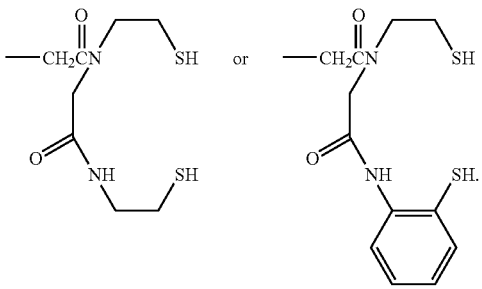

5. The method of claim 3 where $R_8$ is —($CH_2$)$_2$CONHphenyleneCH$_2$DTPA.

6. The method of claim 5 where $R_2$ is —$CH_3$ and $R_5$ is —$CH_2CH_3$.

7. The method of claim 1 where $R_6$ is —$N(R_{10})$—.

8. The method of claim 7 where $R_6$ is —$N(R_{10})$— where $R_{10}$ is hexyl.

9. A method for MR imaging comprising injecting a Technetium$^{99m}$ complex of the compound of claim 2 followed by MR imaging.

10. A method for MR imaging comprising injecting an Indium$^{111}$ complex of the compound of claim 3 followed by MR imaging.

11. A method for MR imaging comprising injecting a Gadolinium(III) complex of the compound of claim 3 followed by MR imaging.

12. A method for MR imaging comprising injecting a compound of claim 9 wherein the compound is a $^{99m}$Tc bisaminoethanethiol analog of HPPH followed by MR imaging.

13. A method for MR imaging comprising injecting a compound of claim 10 wherein the compound is a $^{111}$In aminophenyl DTPA analog of HPPH followed by MR imaging.

14. A method for MR imaging comprising injecting a compound of claim 11 wherein the compound is HPPH-Gd (III)aminophenylDTPA followed by MR imaging.

15. A method for MR imaging comprising injecting a compound of claim 11 wherein the compound is purpurin 18 imide-Gd(III)aminophenylDTPA followed by MR imaging.

16. A method for MR imaging comprising injecting a compound of claim 11 wherein the compound is a Gd(III) aminophenylDTPA analog of bacteriochlorin followed by MR imaging.

* * * * *